United States Patent

Haddock et al.

[11] Patent Number: 5,769,807
[45] Date of Patent: Jun. 23, 1998

[54] IV CATHETER ADHESIVE DRESSING

[75] Inventors: Teresa Haddock, Cranbury, N.J.; Arthur S. Hill, Arlington, Tex.; Shmuel Dabi, Highland Park, N.J.

[73] Assignee: Chicopee, Inc., North Charleston, S.C.

[21] Appl. No.: 541,982

[22] Filed: Oct. 10, 1995

Related U.S. Application Data

[63] Continuation of Ser. No. 308,015, Sep. 16, 1994, abandoned, which is a continuation of Ser. No. 72,622, Jun. 4, 1993, abandoned, which is a continuation of Ser. No. 943,263, Sep. 10, 1992, abandoned.

[51] Int. Cl.$^6$ .................................................. A61F 13/00
[52] U.S. Cl. ........................... 602/52; 424/433; 602/58; 604/307
[58] Field of Search ................................. 602/41, 42, 52, 602/55, 58, 904, 903; 604/180, 307; 424/433

[56] References Cited

U.S. PATENT DOCUMENTS

| | | | |
|---|---|---|---|
| 3,039,893 | 6/1962 | Bonigan, Jr. et al. | 602/54 |
| 4,357,827 | 11/1982 | McConnell | 73/73 |
| 4,541,426 | 9/1985 | Webster | 602/42 |
| 4,657,006 | 4/1987 | Rawlings et al. | 602/47 |
| 4,875,473 | 10/1989 | Alvarez | 602/42 |
| 5,160,315 | 11/1992 | Heinecke et al. | 602/57 |

*Primary Examiner*—Michael Powell Buiz
*Assistant Examiner*—Chalin Smith
*Attorney, Agent, or Firm*—Juettner Pyle Lloyd & Piontek

[57] ABSTRACT

A surgical dressing consisting of a film which carries an adhesive layer wherein the film has a hydration rate of at least 0.1 g/in$^2$/min.; becomes saturated when in contact with water in 3 minutes or less and absorbs at least its own weight of water. The film comprises a polyethylene oxide and a polymer or polymers selected from an ether based polyurethane and a polyether block amide. The dressing finds special use as a IV catheter site cover.

6 Claims, 1 Drawing Sheet

IV CATHETER ADHESIVE DRESSING

This is a continuation of Ser. No. 08/308,015 filed Sept. 16, 1994, now abandoned which is a continuation of Ser. No. 08/072,622 filed Jun. 4, 1993, abandoned, which is a continuation of Ser. No. 07/943,263, filed Sept. 10, 1992, abandoned.

FIELD OF THE INVENTION

This invention relates to an adhesive dressing for use where high moisture vapor transmission is desirable. This invention particularly relates to an adhesive composite for use as a medical dressing on exuding wounds. The invention relates even more particularly to an IV Catheter adhesive dressing.

BACKGROUND OF THE INVENTION

Moisture vapor permeable thin films coated with adhesive are known to be suitable for use as surgical dressings. They have found use as a covering for burns, donor sites, surgical incisions, intravenous IV catheter sites and the like. The known dressings have proved useful because they keep out bacteria owing to the microscopically continuous nature of the film and the adhesive layer, but do not cause maceration of the skin to which they are applied because both the film and the adhesive layer have high moisture vapor transmission rates (MVTR). One problem with presently available high MVTR dressings is that the MVTR is not high enough for some uses. It would be desirable to have a higher MVTR for a dressing covering an IV catheter site. Condensed moisture is occasionally found under film dressings over IV catheter hubs and such moisture is associated with an increased risk of bacterial colonization of the catheter site.

In extreme cases, diaphoretic patients or fluid leakage from the IV line will collect at the site and form a blister. The MVTR of dressings used to cover exuding wounds is purposefully limited so that the wound is not allowed to become dry due to the excessive transfer of moisture. This is not a problem with catheter sites. Since there is no exuding wound to dry out, it is desirable to have an extremely high MVTR so as to remove leaking liquid which may cause a blister under the dressing and also to maintain the catheter site as dry as possible so as to reduce the risk of infection. The presence of a liquid blister can cause adhesion to the skin failure which in turn can allow bacteria entry.

A second problem which can occur with presently available dressings is that the adhesive layer must be applied in an open pattern so as to allow sufficient moisture/film contact area to effect the necessary moisture vapor transmission. Currently available film dressings have up to 30% or even greater open area to effect the necessary moisture vapor transfer. The pattern adhesive application is a costly process and the resultant product may provide channels for liquid leakage and/or bacterial invasion.

It has now been found that if the rate of hydration of the film is sufficiently great the adhesive layer may have as little as 3% open area and still allow the dressing to be fully functional. With hydrophilic films which have a hydration rate of at least 0.1 g/sq. in./min., which absorb liquid in amount at least equal to their own weight, and which when in contact with liquid become saturated in 3 minutes or less, the MVTR of the dressing is independent of the adhesive layer surface coverage between 3% and 40% open area. This means that the adhesive may be applied in essentially a continuous coating via a less expensive process. It also means the dressing product has more adhesive contact area with the skin of the user and is less likely to leak and to fail, permitting bacterial intrusion.

It is, therefore, an object of the present invention to provide a surgical dressing for use with a catheter.

It is a further object of the invention to provide a catheter dressing which has a sufficiently fast rate of hydration so that the dressing may have an adhesive coating with as little as 3–10% open area.

It is yet a further object of this invention to provide a catheter dressing which has a hydration rate of at least 0.1 g./sq.in./min. and which when in contact with liquid becomes saturated within 3 minutes and which when saturated holds at least its own weight in liquid.

It is yet a further object of this invention to provide a catheter dressing which has a MVTR of at least 2000 g./m$^2$/day when in contact with moisture vapor and a MVTR of greater than 3,000 g/m$^2$/day when in contact with water.

PRIOR ART

Moisture vapor permeable adhesive coated thin films are disclosed in U.S. Pat. No. 4,595,001, U.S. Pat. No. 4,798,201; U.S. Pat. No. 3,645,835 and European Patent Application 0437944.

European patent application 0437944 requires at least three layers comprising a backing layer, a high moisture vapor transmission layer, and a skin contacting adhesive layer.

A pressure sensitive adhesive material comprising a backing material and a pressure sensitive adhesive is disclosed in U.S. Pat. No. 3,645,835. The material has a moisture vapor permeability of at least 300 g/m$^2$/24 hrs.

U.S. Pat. No. 4,595,001 is to a surgical dressing which consists essentially of a film which carries an adhesive layer. The film is continuous and comprises a polymer which in contact with water has a higher moisture vapor permeability (MVP) than when in contact with moisture vapor. The dressing has a MVP of not less than 2500 g/m$^2$ when the adhesive layer is in contact with water and has a MVP of not more than 2000 g/m$^2$ when the adhesive is in contact with moisture vapor.

U.S. Pat. 4,798,201 also discloses a surgical dressing which consists essentially of a film which carries an adhesive layer. In this instance the dressing has a MVP of not less than 2500 g/m$^2$ when the adhesive layer is in contact with water and a MVP of not more than 2000 g/im$^2$ when the adhesive is in contact with moisture vapor.

The dressings of the prior art have upper limits on the MVP so that the dressing does not dry out the exuding wound site. The prior art dressings require significant open area in the adhesive layer so as to achieve the required MVP for wound management.

BRIEF DESCRIPTION OF THE DRAWINGS

The invention will be more clearly understood by reference to the following detailed description and the accompanying drawings in which.

DETAILED DESCRIPTION OF THE INVENTION

Figure 1:
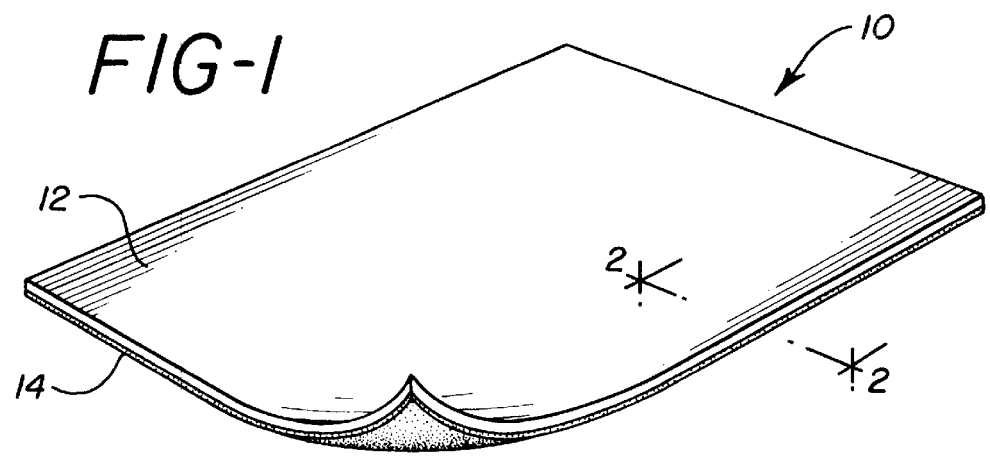
FIG. 1 is a perspective of the adhesive dressing of the invention, with one corner of the dressing being turned so as to show the lower surface thereof.
Figure 2:
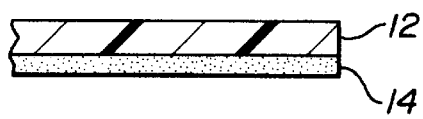
FIG. 2 is a cross-section taken along line 2—2 of FIG. 1.

Referring now to the drawings, FIG. 1 shows in perspective a dressing 10 comprising a film layer 12 coated with an adhesive layer 14. FIG. 2 is a cross sectional view of the dressing 10 taken along line 2—2 of FIG. 1.

Figure 3:
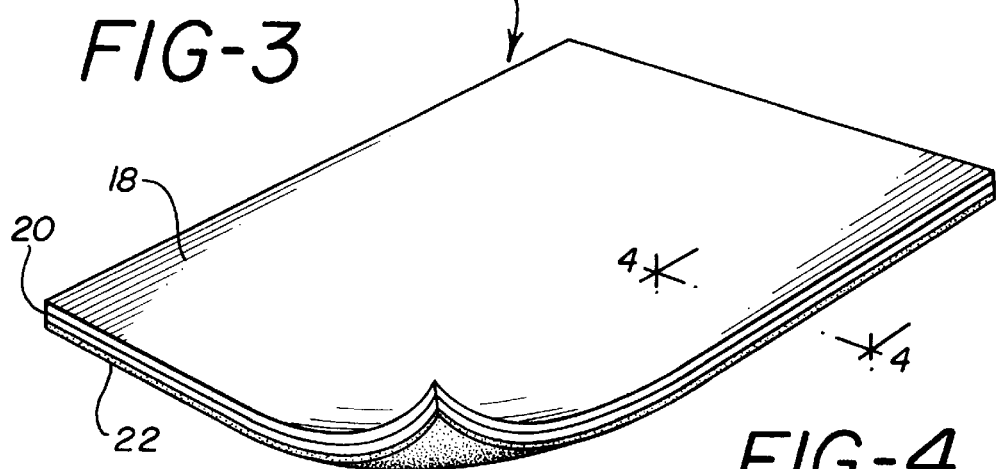
FIG. 3 is a perspective of another dressing of the invention.
Figure 4:
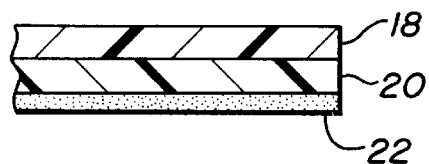
FIG. 4 is a cross-section taken along line 4—4 of FIG. 3.

FIG. 3 shows another embodiment of this invention comprising a three layer dressing 16 wherein a coextruded film comprising a top protective layer 18 and a bottom absorbing film layer 20 is coated with an adhesive 22. FIG. 4 is a cross sectional view of the dressing 16 taken along the line 4—4 of FIG. 3.

The surgical dressing 10,16 of this invention consists essentially of a film 12,20 which carries an adhesive layer 14,22 wherein the film has a hydration rate of at least 0.1 g/in$^2$/min., becomes saturated when in contact with water in 3 minutes or less, absorbs at least its own weight of water, and which when in contact with water has a higher moisture vapor transmission rate (MVTR) than when in contact with moisture vapor. The adhesive layer 14,22 is porous in that it has an essentially uniformly spaced patternless open area. The surgical dressing of this invention has an MVTR of not less than 3000 g/m$^2$/day when in contact with water, and an MVTR of at least 2000 g/m$^2$/day when in contact with moisture vapor.

The hydrophilic film 12,20 when fully hydrated will contain at least its own weight, i.e., 100% of water. More preferably the film will contain 100–150% water and even more preferred, the film will contain 150–250% water.

The hydrophilic film may comprise any synthetic polymer, copolymer, graft or block copolymer, or polymer blend which provides the required hydration rate, absorbency and MVTR. Ideally, the polymers should be melt processable to allow manufacture by melt extrusion, but such films may also be produced by casting the film from solvent.

The preferred films are made from polymer melt blends which have balanced hydrophilic and hydrophobic properties. A preferred melt blend is an alloy of an ether based polyurethane (PU) and a high molecular weight polyethylene oxide (PEO) wherein the PEO has a molecular weight of greater than 100,000. The concentration of PEO can vary from 5 to 50% of the alloy by weight. The preferred concentration of PEO is from 10 to 30%. The preferred molecular weight of the PEO is 100,000 to 1,000,000. In order to obtain a uniform blend or alloy, the polyurethane must have a polyether linkage on the polymer backbone. The polyurethane controls the alloy film strength. To have a desired strength the polyurethane must have a maximum melt index of 20 g/min. at 190° C.

Another polymer alloy usable in this invention comprises polyurethane, PEO and a polyether block amide (PEBA). The urethane and PEO are as described above. The PEO may be varied between 5 and 50% by weight with the remainder of the alloy being divided between the PU and the PEBA factions.

The polymer alloys are extruded by standard procedures well known in the art into single layer films having a thickness of 1 mil (0.001 inch) to 5 mil.

Coextruded, i.e., two layer films as shown in FIG. 3 and 4 may also be employed in this invention. In this case a relatively hydrophobic layer is used as a top layer 18. The top layer is the layer which does not contact the adhesive and is the layer which in use is the furthest removed from the skin. The hydrophobic layer is used to protect the bottom hydrophilic layer 20. By varying the relative thickness of the two layers, the MVTR can be controlled and the desired level achieved. Polyurethane, PEBA, polyether based polyester or blends of hydrophobic and hydrophilic resins can be used as the top layer. The bottom layer must be more hydrophilic and is as described hereinbefore.

Due to the rapid rate of hydration of the films of this invention and due to the absorbent capacity of the films, the porous adhesive coating applied to the film may have as little as 3% open area. It is preferred that the adhesive layer have an open area of 3–10%. By open area is meant that portion of the film surface in which there is no adhesive covering. It has been found that by using the films of this invention in an IV Catheter dressing that the MVTR of the dressing is not influenced by the adhesive coverage when the open area is between 3 and 40%.

The adhesive may be any of the pressure sensitive adhesives well known in the art that are useful for skin contact. The preferred material is an acrylic pressure sensitive adhesive. The adhesive is generally employed at a mass per unit area of 10 to 100 g/m$^2$ and it is preferred to apply 15 to 40 g/m$^2$.

Since an adhesive coating with low open area is preferred, the adhesive can be applied by a conventional reverse roll coating process. By adding a small amount of an evaporatible nonsolvent to the adhesive system, the open area of the coated material can be controlled. For example, adding a small amount of hydrocarbon solvent to a water based adhesive system or by adding a small amount of water to a solvent based adhesive system will, on drying, provide pores or open area in the adhesive layer due to the different evaporation rates.

The following examples illustrate the practice of the invention.

EXAMPLE 1

An ether based polyurethane (PU) resin identified as Estane 58630 and supplied by B. F. Goodrich is mixed with a polyethylene oxide (PEO) resin, Polyox N-750 as supplied by Union Carbide. The mixture contains 80% by weight PU and 20% by weight of PEO. The polymers are melt blended by extruding using a twin screw extruder at a melt temperature of 180° C. A string die is used which discharges into a cold water quenching tank. The string is chopped into pellets. The blended pellets are fed to a film extruder which has an L/D of 24/1 and operates at a melt temperature of 180° C. using a standard film die. A 2 mil (0.002 inch) film is prepared, air cooled and rolled up. The extruders for melt blending and for film production are operated in a standard manner well known to those skilled in the art.

A commercially available solvent based acrylic adhesive, Monsanto 2674, is coated on release paper by reverse roll coating. The adhesive is coated at a weight of 20 g/m$^2$. The coated adhesive has an open area of 30%. The release paper containing the adhesive coating is combined with the film to provide a layered structure with the adhesive between the release paper and the film. The coating and the laminating process are both well known to those skilled in the art.

The film adhesive laminate with release paper is then die cut to appropriate size for dressing use. The dressing is tested for MVTR by the Gravimetric Absorvency Tester (GAT). Method hereinafter described and found to have an MVTR of 1650 g/m$^2$/day. The film has a hydration rate of 0.37 g/in$^2$/min and saturates within 0.2 minutes.

EXAMPLE 2

The procedure of Example 1 is followed except the film polymer blend is 100% Estane 58630. The same adhesive is used and the coating is applied so as to provide essentially a continuous coating with no open area. This commercially available product when tested showed no liquid absorption and did not hydrate.

EXAMPLE 3

The procedure of Example 1 is followed except the film polymer blend is 100% Estane 58630. The same adhesive coating at the same level and open area is used. The dressing when tested has an MVTR of 275 g/m²/day. It did not absorb liquid and did not hydrate.

EXAMPLE 4

The same procedure as Example 1 is followed except the resin composition comprises by weight 40% Pebax 4011, a polyether block amide supplied by Atochem, 30% Pellethane 2103-70A, a polyether based polyurethane supplied by Dow Chemical, and 30% Polyox N-750, a polyethylene oxide supplied by Union Carbide. Using the same adhesive and coating as Example 1, the dressing is tested by the GAT method has a MVTR of 4500 g/m²/day. When fully hydrated it absorbed 190% its own weight of water.

EXAMPLE 5

Using the same film and adhesive as Example 4 except the adhesive used here was a water based acrylic with a small amount of hexane present which on drying yielded an open area of 3.8%. The MVTR of this dressing was found to be 4750 g/m²/day. When fully hydrated the dressing absorbed 190% its own weight of water.

EXAMPLE 6

Following the same procedure as Example 1 except that the film resin formulation is by weight 60% Pebax 4011, 30% Pellethane 2103-70A, and 10% Polyox N-750 the resultant dressing has an MVTR of 4650 g/m²/day. This dressing when fully hydrated absorbed 115% its own weight of water.

EXAMPLE 7

The same film and procedure of Example 6 is used except the applied adhesive has an open area of 5%. This dressing has a MVTR of 4340 g/m²/day. When fully hydrated this dressing absorbed 115% its own weight of water.

EXAMPLE 8

A dressing is prepared using the procedure of Example 1 except the film comprises by weight 50% Pebax 4011, 30% Pellethane 2103-70A and 20% Polyox N-80 (M.W. 200,000). This dressing has a MVTR of 5890 g/m²/day. When fully hydrated the dressing absorbed 168% its own weight of liquid.

EXAMPLE 9

A coextruded two layered film was prepared using a standard extruder process. The top protective layer was 100% Pebax 5533 supplied by Atochem and the bottom and adhesive contacting layer was the same composition as the film of Example 5. The extruded film was 0.0018 inches thick. The top layer comprised 20% of the film thickness and the bottom layer comprised the remaining 80% of the film thickness. The film was adhesive coated as in Example 5. The resultant dressing had an MVTR of 2600 g/m²/day.

When fully hydrated the dressing absorbed 116% of its own weight of liquid.

TABLE 1

| Film | Adhesive Open Area (%) | MVTR g/m²/day | Time for Film to Reach Saturation (min) | Rate of Film Hydration g/in²/min |
| --- | --- | --- | --- | --- |
| Example 1 | 30 | 1650 | 0.3 | 0.37 |
| Example 2 | 0 | 125 | Did not Absorb | No Hydration |
| Example 3 | 30 | 275 | Did not Absorb | No Hydration |
| Example 4 | 30 | 4500 | 2 | 0.13 |
| Example 5 | 3.8 | 4750 | 2 | 0.13 |
| Example 6 | 30 | 4650 | 0.7 | 0.28 |
| Example 7 | 5 | 4340 | 0.7 | 0.28 |
| Example 8 | 30 | 5890 | 0.5 | 0.37 |
| Example 9 | 6 | 2600 | 0.3 | 0.50 |

MVTR Determination

The Moisture Vapor Transmission Rate (MVTR is determined using the "Gravimetric Absorbency Tester" of U.S. Pat. No. 4,357,827 which is incorporated herein by reference. MVTR is determined using the apparatus and test cell shown in FIGS. 1 and 4 of the '827 patent. A chart recorder is connected to the weighing device (16 of FIG. 1 of the '827 patent) to automatically record the weight gain of the test specimen. All tests are done at a room temperature of 25° C. using a 1% saline solution as the liquid. The test cell (FIG. 4 of the '827 patent) employs a porous plate with a diameter of 9 cm. and pore size of 25–40 microns. The porous plate is maintained at 0.5 cm. higher than the liquid level so as to provide a negative pressure during the sample absorption process.

Figure 5:
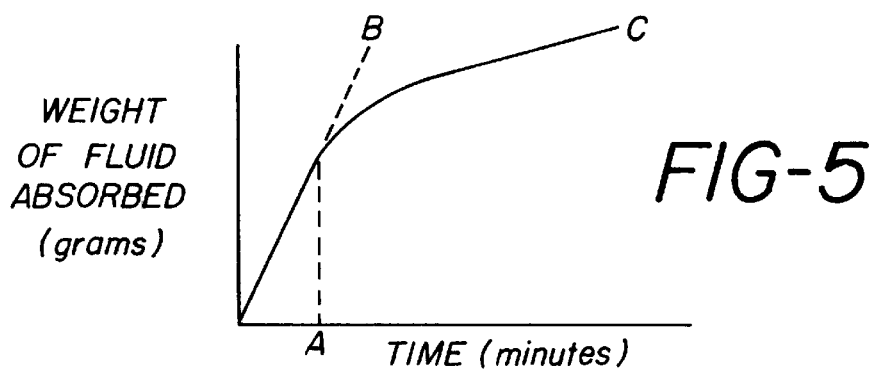
FIG. 5 is a typical response curve obtained in the MVTR determination.

The test specimen, either dressing or fiber, is placed on the porous plate and the liquid is introduced to the plate. The weight change with time is recorded. The resultant chart is shown in FIG. 5 wherein:

A is taken as the time for film saturation as determined by reading the inflection point.

B is the rate of film hydration.

C is MVTR.

As can be seen the dressing (film) first goes through a rapid absorption as the film is hydrated. This hydration is the initial steep curve shown in the figure above. After the film is saturated with liquid, a constant evaporation takes place.

The slope of this part of the curve is defined as the MVTR as calculated from the test specimen area, and the weight change with time.

For the test of the rate of film hydration, the test specimen is held in contact with the porous plate by placing a 100 g. glass plate on top of the specimen.

Degree of Hydration

To determine the degree of hydration of the film a preweighed dressing is immersed in water at room temperature for ½ hour. The test specimen is then removed from the water, blotted to remove free water using a paper towel and is immediately weighted. The weight gain is determined by the following equation:

$$\% \text{ Hydration} = \frac{\text{Wet Weight} - \text{Dry Weight}}{\text{Dry Weight}} \times 100$$

where wet weight=weight of specimen after immersion.
dry weight=weight of specimen before immersion.
What is claimed is:
1. A surgical dressing which consists essentially of a continuous film in direct contact with an adhesive layer for securing the dressing to the human body wherein a) said film has a hydration rate of at least 0.1 $g/in^2/min$ becomes saturated when in contact with liquid water, has a higher MVTR than when in contact with water vapor in the absence of liquid water, said film being coextruded and comprising a hydrophobic top layer and a hydrophilic bottom layer, wherein said adhesive layer is in direct contact with said hydrophilic layer, b) said adhesive layer is porous and allows access of water to the film when water is in contact with said adhesive layer and wherein said dressing has a MVTR of not less than 3000 $g/m^2/day$ when in contact with liquid water and a MVTR greater than 2000 $g/m^2/day$ when in contact with water vapor but not in contact with liquid water.

2. The dressing of claim 1 wherein said film when fully hydrated contains at least its own weight of water.

3. The dressing of claim 1 wherein said film when fully hydrated contains 1 to 1½ times its own weight of water.

4. The dressing of claim 1 wherein said film when fully hydrated contains 1½ to 2½ times its own weight of water.

5. The dressing of claim 1 wherein said film has a thickness of 1 mil (0.001 inch) to 5 mil.

6. The dressing of claim 1 wherein said adhesive is an acrylic pressure sensitive adhesive.

* * * * *